(12) United States Patent
Szewczyk et al.

(10) Patent No.: US 9,498,418 B2
(45) Date of Patent: Nov. 22, 2016

(54) ABRADABLE FILMS FOR USE IN ORAL CARE

(71) Applicant: Colgate-Palmolive Company, New York, NY (US)

(72) Inventors: Gregory Szewczyk, Flemington, NJ (US); Neeta Atul Patel, Monmouth Junction, NJ (US); Suzanne Jogun, Wayne, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 14/651,622

(22) PCT Filed: Dec. 14, 2012

(86) PCT No.: PCT/US2012/069900
§ 371 (c)(1),
(2) Date: Jun. 11, 2015

(87) PCT Pub. No.: WO2014/092738
PCT Pub. Date: Jun. 19, 2014

(65) Prior Publication Data
US 2015/0328125 A1    Nov. 19, 2015

(51) Int. Cl.
*A61K 8/34*   (2006.01)
*A61K 9/70*   (2006.01)
*A61K 8/49*   (2006.01)
*A61Q 11/00*  (2006.01)
*A61K 8/73*   (2006.01)
*A61K 8/81*   (2006.01)
*A61K 8/02*   (2006.01)

(52) U.S. Cl.
CPC ............ *A61K 8/345* (2013.01); *A61K 8/0254* (2013.01); *A61K 8/4993* (2013.01); *A61K 8/731* (2013.01); *A61K 8/8129* (2013.01); *A61Q 11/00* (2013.01); *A61K 2800/43* (2013.01); *A61K 2800/45* (2013.01); *A61K 2800/56* (2013.01); *A61K 2800/805* (2013.01)

(58) Field of Classification Search
CPC .... A61K 8/731; A61K 2800/43; A61K 9/70; A61Q 11/00
See application file for complete search history.

(56) References Cited

U.S. PATENT DOCUMENTS

| 3,662,059 A | 5/1972 | Wiesner et al. |
| 3,944,661 A * | 3/1976 | Colodney ............... A61K 8/25 424/49 |
| 4,150,106 A | 4/1979 | Assal et al. |
| 4,335,102 A | 6/1982 | Nakashima et al. |
| 6,136,297 A | 10/2000 | Sagel et al. |
| 6,479,036 B1 | 11/2002 | Stanier et al. |
| 6,669,929 B1 | 12/2003 | Boyd et al. |
| 7,763,235 B2 | 7/2010 | Boyd et al. |
| 2002/0034479 A1 | 3/2002 | Green |
| 2004/0101489 A1 | 5/2004 | Nathoo |
| 2004/0219111 A1 | 11/2004 | Kim et al. |
| 2004/0247646 A1 | 12/2004 | Ivory et al. |
| 2005/0019273 A1 | 1/2005 | Boyd et al. |
| 2005/0019275 A1 | 1/2005 | Sagel et al. |
| 2006/0134020 A1 | 6/2006 | Robinson et al. |
| 2007/0020201 A1 | 1/2007 | Boyd et al. |
| 2007/0148213 A1 | 6/2007 | Ibrahim et al. |
| 2007/0264487 A1 | 11/2007 | Georgiades |
| 2008/0138369 A1 | 6/2008 | Boyd et al. |
| 2008/0187497 A1 | 8/2008 | Agarwal et al. |
| 2008/0187498 A1 | 8/2008 | Francis |
| 2008/0245678 A1 | 10/2008 | Gantenberg |
| 2008/0247967 A1 | 10/2008 | Sagel |
| 2008/0247968 A1 | 10/2008 | Sagel |
| 2008/0247969 A1 | 10/2008 | Glandorf |
| 2008/0247970 A1 | 10/2008 | Gantenberg |
| 2008/0248072 A1 | 10/2008 | Glandorf |
| 2008/0248073 A1 | 10/2008 | Gantenberg |
| 2008/0260836 A1 * | 10/2008 | Boyd ..................... A61K 8/02 424/488 |
| 2009/0060597 A1 | 3/2009 | Yoshida et al. |
| 2009/0098188 A1 | 4/2009 | Staab |

(Continued)

FOREIGN PATENT DOCUMENTS

| EP | 0255210 | 9/1992 |
| EP | 1417895 | 5/2006 |
| EP | 2116219 | 11/2009 |

(Continued)

OTHER PUBLICATIONS

International Search Report and Written Opinion in International Application No. PCT/US2012/069900, mailed Nov. 18, 2013.

(Continued)

*Primary Examiner* — Frederick Krass
*Assistant Examiner* — Tracy Liu

(57) ABSTRACT

The present invention relates to abradable films useful, e.g., in dentifrice formulations, wherein the film is stable in formulation, but abrades to release pigment or oral care active components upon brushing. The invention provides, e.g., an orally acceptable, water insoluble film which does not dissolve under formulation conditions but disintegrates upon brushing, comprising a polymer matrix, plasticizer (e.g., propylene glycol), releasable material (e.g., color or pigment) incorporated therein; and (optionally) nonionic surfactant (e.g. polysorbate), wherein the polymer matrix comprises at least 50%, e.g., at least 75%, of poly(vinyl alcohol), and 50% or less, e.g. 25% or less, of a water-soluble cellulose ether, for example hydroxypropyl methyl cellulose; together with dentifrice comprising such films, and methods of making and using the same.

19 Claims, No Drawings

(56) References Cited

U.S. PATENT DOCUMENTS

2011/0142942 A1* 6/2011 Schobel ............... A61K 9/006
424/489
2011/0150968 A1* 6/2011 Grassi ................. A23L 1/0067
424/439

FOREIGN PATENT DOCUMENTS

| EP | 1843738 | 3/2010 | | |
|---|---|---|---|---|
| EP | 2105122 | 9/2012 | | |
| JP | S6016912 | 1/1985 | | |
| WO | WO 03/000216 | 1/2003 | | |
| WO | WO 2005/123023 | 12/2005 | | |
| WO | WO 2010/114551 | 10/2010 | | |
| WO | WO 2011068513 A1 * | 6/2011 | ............... | A61K 8/02 |
| WO | WO 2012/002946 | 1/2012 | | |
| WO | WO 2013/108384 | 7/2013 | | |

OTHER PUBLICATIONS

Written Opinion in International Application No. PCT/US2012/069900, mailed Jan. 23, 2015.

* cited by examiner

ABRADABLE FILMS FOR USE IN ORAL CARE

BACKGROUND OF THE INVENTION

It is recommended that children brush their teeth for at least 45-60 seconds, and adults for at least 90-120 seconds. Most people, especially children, do not brush their teeth for a sufficient period of time to obtain maximum benefit, and moreover have difficulty accurately estimating the time necessary to brush their teeth.

Toothpaste comprising colored film fragments are known in the art, e.g., as described in U.S. Pat. No. 6,669,929, the contents of which are incorporated herein by reference, but this reference does not address the need for encouraging brushing for an appropriate period. Film fragments as known in the art for such purposes are generally dissolvable in water, that is, they utilize polymer systems that will swell and eventually dissolve when placed in water.

There is a need for improved, consumer-friendly products and methods to encourage users to brush their teeth for a longer period of time.

BRIEF SUMMARY OF THE INVENTION

Prior efforts to improve formulation stability of dentifrice products comprising film fragments and to provide quick dissolution of the fragments upon use focused on controlling the dissolution of the film matrix using various polymer systems. These types of dentifrice products would naturally dissolve when present in the oral cavity for a period of time (e.g. 30-180 seconds) regardless of whether the abrasive action (e.g. brushing the formulation against the teeth or the oral cavity) was supplied to the dentifrice.

There is still a need in the art for a polymer containing film which does not dissolve in the oral cavity, but can release a pigment or color at a desired period of time.

Surprisingly, it is discovered that polymer systems comprising of relatively high levels of poly(vinyl alcohol) not only have extended dissolution and enhanced stability in formulation, but are in fact substantially insoluble under formulation or use conditions. These systems readily and abruptly disintegrate during brushing, to provide fast release of entrapped pigment/color (or other components for which quick release is desired, e.g. flavoring or whitening agents), thereby providing a clear signal and complete release of the material when the desired brushing threshold is reached.

The invention provides an orally acceptable, water insoluble film which does not dissolve under formulation conditions, but disintegrates upon brushing, comprising a polymer matrix, plasticizer (e.g., propylene glycol), releasable material (e.g., color or pigment) incorporated therein (e.g., that is released upon disintegration of the film by mechanical action, e.g., brushing); and (optionally) nonionic surfactant (e.g. polysorbate), wherein the polymer matrix comprises at least 50%, e.g., at least 75%, of poly(vinyl alcohol), and 50% or less, e.g. 25% or less, of a water-soluble cellulose ether, for example hydroxypropyl methyl cellulose (HPMC); as well as dentifrice comprising such films, and methods of making and using the same.

Further areas of applicability of the present invention will become apparent from the detailed description provided hereinafter. It should be understood that the detailed description and specific examples, while indicating the preferred embodiment of the invention, are intended for purposes of illustration only and are not intended to limit the scope of the invention.

DESCRIPTION OF THE INVENTION

The following description of the preferred embodiment(s) is merely exemplary in nature and is in no way intended to limit the invention, its application, or uses.

The invention thus provides, in a first embodiment, an orally acceptable, water-insoluble film (Film 1), which disintegrates upon brushing in the presence of water, comprising
a polymer matrix, a releasable material incorporated therein, and a plasticizer, wherein the polymer matrix comprises at least 50% of poly(vinyl alcohol), and 50% or less of a water-soluble cellulose ether;

for example, 1.1. Film 1 wherein the releasable material is a pigment or combination of pigments, e.g., that is released upon disintegration of the film by mechanical action, e.g., brushing; e.g., wherein the pigment or combination of pigments is selected from one or more of a red pigment, for example D&C Red 30, a green pigment, for example Pigment Green 7, a yellow pigment, e.g. (Natpure LC 128 Yellow, from Sensient Co.), a blue pigment, for example a phthalocyanine, for example Pigment Blue 15:

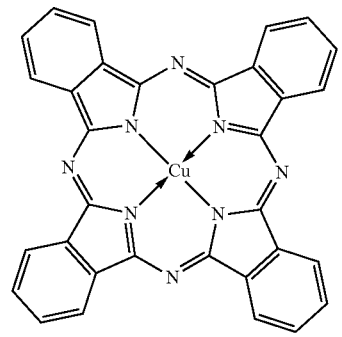

1.2. Film 1 or 1.1 wherein the water-soluble cellulose ether is a hydroxyalkyl cellulose, e.g., selected from hydroxypropyl methyl cellulose, hydroxyethylpropyl cellulose, hydroxybutyl methyl cellulose, carboxymethyl cellulose and mixtures thereof. In one embodiment of the film, the water soluble cellulose ether is hydroxypropyl methyl cellulose;

1.3. Any of the foregoing films wherein the poly(vinyl alcohol) comprises the structure —(—CH$_2$CH(OH)—)$_n$—, for example wherein n is an integer 500-2500, e.g., 1000-2000, e.g, about 1400; e.g., having a weight average molecular weight ($M_w$) of 20-120 kD, e.g., 35-100 kD or 50-70 kD, e.g., about 61 kD, e.g., Mowiol® 10-98 (PVA 10-98);

1.4. In an alternative embodiment of the foregoing films, the poly(vinyl alcohol) have the properties described in 1.3 above and also have a degree of hydrolyzation of at least 50%, e.g. 85-99%, e.g. PVA 5-88 ($M_w$=about 37 kD and degree of hydrolyzation of 88%) or PVA 10-98 ($M_w$=about 61 kD and degree of hydrolyzation of 98%).

1.5. Any of the foregoing films wherein the water-soluble cellulose ether is hydroxypropyl methyl cellulose (HPMC), e.g., a low viscosity HPMC, e.g., having a viscosity at 2% concentration in water at 20° C. of 2-20 mPa*s (cP), e.g., 4-6 mPa*sec, e.g., as measured with an Ubbelohde viscometer, for example HPMC E5 (Methocel® E5);

1.6. Any of the foregoing films wherein the plasticizer is a polyalcohol, e.g., sorbitol, propylene glycol, glycerol, low molecular weight polyethylene glycol, e.g., PEG 200, or mixtures thereof e.g., in an amount effective to provide plasticity to the film, e.g., about 10-30%, e.g., 15-25% by dry weight of the film;

1.7. Any of the foregoing films wherein the plasticizer is propylene glycol;

1.8. Any of the foregoing films comprising a non-ionic surfactant or emulsifier, e.g., a polysorbate, e.g., polysorbate 80 (also known as polyoxyethylene(20) sorbitan monooleate, available commercially e.g., as Tween® 80), e.g., in an amount of about 1-5% by dry weight of the film;

1.9. Any of the foregoing films wherein the film is coated by a powder coating which comprises a pigment, e.g., wherein the powder coating comprises a white powder pigment, e.g., comprising particles of titanium dioxide or $Ca_2P_2O_7$; or wherein the powder coating comprises a red powder pigment, e.g., comprising particles of red iron oxide or D&C Red 30;

1.10. Any of the foregoing films wherein the releasable material comprises a water-insoluble material, e.g., a water-insoluble antimicrobial agent, e.g., selected from triclosan and zinc oxide;

1.11. Any of the foregoing films wherein the film is substantially disintegrated after a period of greater than 30 seconds and less than 180 seconds of brushing in the presence of water; in another embodiment of the invention, the film is substantially disintegrated from a range selected from the group consisting of about 45 seconds to about 150 seconds, about 30 seconds to about 75 seconds, about 45 seconds to about 60 seconds, and about 90 seconds to about 120 seconds. The films are also characterized in that in the films do not disintegrate in the absence of brushing for the time periods mentioned above.

1.12. Any of the foregoing films wherein the polymer matrix comprises at least 75%, e.g. at least 90% of poly(vinyl alcohol), and 25% or less, e.g. 10% or less, of a water-soluble cellulose ether;

1.13. Any of the foregoing films wherein the polymer matrix comprises 50%-100%, e.g. 75%-90% of poly (vinyl alcohol), and 1-50%, e.g. 10%-25% of a water-soluble cellulose ether;

1.14. Any of the foregoing films wherein the average thickness of the film is 1-3 mil;

1.15. Any of the foregoing films comprising

| Component | Exemplary ingredient | Percent by weight of dry film |
|---|---|---|
| Water soluble cellulose ether (polymer matrix) | e.g., hydroxypropylmethyl cellulose (HPMC) | 1-10%, e.g. about 3-7% |
| Poly(vinyl alcohol) (polymer matrix) | e.g., poly(vinyl alcohol), e.g., weight avg. MW ($M_W$) 50-70-kD | 30-60%, e.g. about 40-50% |
| Releasable material | e.g., pigment, e.g., Pigment Blue 15 | 20-60%, e.g., about 35-45% |
| Plasticizer | e.g., propylene glycol | 10-30% e.g., about 15-20% |
| Surfactant | e.g., polysorbate 80 | 1-5%, e.g., 2-3% |

1.16. Any of the foregoing films prepared by making an aqueous slurry of the ingredients as set forth in the foregoing embodiments, e.g., an aqueous slurry of polyvinyl alcohol, water-soluble cellulose ether, releasable material, plasticizer, and optionally surfactant, and drying the slurry to form a film.

1.17. Any of the foregoing films wherein by "water insoluble" is meant that the film will not dissolve when placed in water sufficient to cover the film, at room temperature, for a period of at least 24 hours.

The invention further provides an oral care product, e.g., a dentifrice, for example a toothpaste, e.g., a clear gel toothpaste, comprising particles, e.g. squares, stars, flakes or fragments, e.g., 1-10 mm, e.g. 2-4 mm in diameter, of any of Film 1, et seq., wherein upon application to the oral cavity and brushing, the film disintegrates and releases the releasable material following at least 30 seconds and not more than about 180 seconds, e.g., about 45-60 seconds in a toothpaste for use by a child and about 90-120 seconds in a toothpaste for use by an adult; for example wherein the releasable material is a pigment the release of which provides a color signal to the user of adequate brushing. If used in animals or pets, veterinary pastes or chewables may be used in lieu of a dentifrice.

For example, in one embodiment, the toothpaste is a clear gel, in which the film particles can be seen clearly. The film particles may be, for example, small squares 2-4 mm across. They may be all one color or assorted colors, the color being imparted by any pigment in the film, and/or by a powder coating where present, and the film may contain a high concentration of pigment. After a period of brushing, e.g., at least 30 seconds, the film is disrupted, and the clear gel toothpaste is suddenly colored by the pigment, signaling to the user that he or she has brushed for an adequate period.

The invention further provides a method of cleaning the teeth comprising brushing with a toothpaste comprising an orally acceptable film, e.g, as described in the preceding paragraphs, e.g., wherein the film is any of Film 1, et seq., for example a. the method wherein the orally acceptable film comprises a pigment in the film matrix and brushing is continued until the film disintegrates and the pigment provides a color signal to the user of adequate brushing, for example, b. the foregoing method when the brushing time before the film disinegrates is between 30 and 180 seconds, e.g., about 45-60 seconds for a toothpaste for use by a child and about 90-120 seconds for a toothpaste for use by an adult.

The invention further provides a method of manufacturing any of Film 1, et seq. comprising making an aqueous slurry of the ingredients as set forth in the foregoing embodiments for Film 1, et seq., e.g., making an aqueous slurry of poly(vinyl alcohol), water-soluble cellulose ether, releasable material, plasticizer, and optionally surfactant, and drying the slurry to form a film.

Orally acceptable: The compositions of the invention are intended for topical use in the mouth, thus components for use in the present invention should be orally acceptable, that is, safe for topical use in the mouth, in the amounts and concentrations provided.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Embodiments of the present invention are further described in the following examples. The examples are merely illustrative and do not in any way limit the scope of the invention as described and claimed.

EXAMPLES

Example 1

Film Formulations

Films are prepared with various proportions of poly(vinyl alcohol) (PVA) and hydroxypropylmethyl cellulose (HPMC) as follows in Table 1:

TABLE 1

| PVA/HPMC ratio | Dissolution time |
|---|---|
| 15/0 | No dissolution (>24hrs) |
| 7.5/7.5 | No dissolution (>24hrs) |
| 5.5/9.5 | 420 sec |

As seen from the above table, the use of PVA 10-98 exclusively provides a formulation wherein the resulting film does not dissolve even after a 24 hours exposure to water. In an HPMC type system, a 1×1 inch swatch placed in water will slowly swell and release the color payload over time. The release from an HPMC system is driven by the hydrophilicity of the polymer as well as the thickness of the film.

Films comprising primarily PVA in the matrix are compared to films with higher levels of HPMC, are shown below in Table 2 (amounts given as percent of ingredients in slurry prior to drying to form the film):

TABLE 2

| Ingredient | Abradable (non soluble) | Water soluble |
|---|---|---|
| HPMC E5 | 2 | 10 |
| PVA 10-98 | 13 | 5 |
| Pigment Blue 15 | 15 | 15 |
| Propylene Glycol | 7 | 7 |
| Polysorbate 80 | 1 | 1 |
| Water (prior to evaporation) | balance | balance |

In an in vitro brushing study, it is seen that, while film formulations containing at least 50% PVA will not swell and dissolve, they will break down upon use from abrasion, thereby releasing the color payload. The abrasion in this test is provided via a toothbrush head that is mechanically driven in a well using a brushing motion in the presence of toothpaste and water.

As those skilled in the art will appreciate, numerous changes and modifications may be made to the embodiments described herein without departing from the spirit of the invention. It is intended that all such variations fall within the scope of the appended claims.

What is claimed is:

1. A dentifrice comprising particles of orally acceptable, water-insoluble film, which disintegrates upon brushing in the presence of water, the film comprising a polymer matrix, a releasable material incorporated therein, and a plasticizer, wherein the polymer matrix comprises at least 50% of poly(vinyl alcohol), and 50% or less of a water-soluble cellulose ether and is further characterized in that the film does not disintegrate in the absence of brushing and wherein the film does not dissolve when placed in water sufficient to cover the film, at room temperature, for a period of at least 24 hours, and upon application to the oral cavity and brushing, the film disintegrates and releases the releasable material following at least 30 seconds and not more than about 180 seconds.

2. The dentifrice according to claim 1, wherein the releasable material is a pigment or combination of pigments.

3. The dentifrice according to claim 1 wherein the water-soluble cellulose ether is a hydroxyalkyl cellulose or mixture of hydroxyalkyl celluloses.

4. The dentifrice according to claim 1 wherein the water-soluble cellulose ether is hydroxypropyl methyl cellulose.

5. The dentifrice according to claim 1 wherein the plasticizer is a polyalcohol selected from sorbitol, propylene glycol, glycerol, polyethylene glycol, and mixtures thereof.

6. The dentifrice according to claim 1 wherein the plasticizer is propylene glycol.

7. The dentifrice according to claim 1, the film further comprising a non-ionic surfactant or emulsifier.

8. The dentifrice according to claim 7 wherein the non-ionic surfactant or emulsifier is a polysorbate.

9. The dentifrice according to claim 1 wherein the film is coated by a powder coating which comprises a pigment.

10. The dentifrice according to claim 1 wherein the releasable material comprises a water-insoluble antimicrobial agent.

11. The dentifrice according to claim 1 wherein the average thickness of the film is 1-3 mil.

12. The dentifrice according to claim 1 wherein the polymer matrix comprises at least 75% of poly(vinyl alcohol), and 25% or less of a water-soluble cellulose ether.

13. The dentifrice according to claim 1, the film comprising:
1-10 wt% water soluble cellulose ether;
30-60 wt% poly(vinyl alcohol);
20-60 wt% releasable material;
10-30 wt% plasticizer; and
1-5 wt% surfactant.

14. The dentifrice according to claim 1, the film comprising:
3-7 wt% hydroxypropylmethyl cellulose (HPMC);
40-50 wt% poly(vinyl alcohol);
35-45 wt% pigment;
15-20 wt% propylene glycol; and
2-3 wt% polysorbate 80.

15. The dentifrice of claim 1 wherein the releasable material is a pigment, the release of which provides a color signal to the user of adequate brushing.

16. The dentifrice of claim 1 which is a clear gel toothpaste, in which the film particles can be seen.

17. A method of cleaning the teeth, comprising brushing with a dentifrice according to claim 1, and thereby disrupting the film and causing release of the releasable material.

18. The method of claim 17 wherein the orally acceptable film comprises a pigment in the film, and brushing is continued until the film disintegrates and the pigment provides a color signal to the user of adequate brushing.

19. A method of manufacturing a film according to claim 1 comprising making an aqueous slurry of poly(vinyl alcohol), water-soluble cellulose ether, releasable material, plasticizer, and optionally surfactant, and drying the slurry to form a film.

* * * * *